(12) United States Patent
Kim et al.

(10) Patent No.: US 11,571,121 B2
(45) Date of Patent: Feb. 7, 2023

(54) TERMINAL USE PATTERN INFORMATION COLLECTION MANAGEMENT METHOD AND SYSTEM

(71) Applicant: Industry-Academic Cooperation Foundation, Yonsei University, Seoul (KR)

(72) Inventors: Min Kim, Seoul (KR); Wung Rak Choi, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 405 days.

(21) Appl. No.: 16/635,949

(22) PCT Filed: Jul. 27, 2018

(86) PCT No.: PCT/KR2018/008526
§ 371 (c)(1),
(2) Date: Jan. 31, 2020

(87) PCT Pub. No.: WO2019/027184
PCT Pub. Date: Feb. 7, 2019

(65) Prior Publication Data
US 2020/0337549 A1    Oct. 29, 2020

(30) Foreign Application Priority Data

Aug. 3, 2017  (KR) .......................... 10-2017-0098621

(51) Int. Cl.
*A61B 3/00* (2006.01)
*G06F 11/34* (2006.01)
*G06T 5/00* (2006.01)

(52) U.S. Cl.
CPC ........ *A61B 3/0025* (2013.01); *G06F 11/3438* (2013.01); *G06T 5/002* (2013.01)

(58) Field of Classification Search
CPC ... A61B 3/0025; G06F 11/3438; G06F 3/013; G06F 3/04845; G06F 3/04842; G06F 2203/04806; G06F 3/0484; G06T 5/002
See application file for complete search history.

(56) References Cited

U.S. PATENT DOCUMENTS

2011/0035675 A1* 2/2011 Kim ...................... G06Q 50/32
                                                        715/745
2014/0355830 A1  12/2014 Park et al.
(Continued)

FOREIGN PATENT DOCUMENTS

JP      2007097695 A    4/2007
JP      2011123501 A    6/2011
(Continued)

*Primary Examiner* — Vu Le
*Assistant Examiner* — Winta Gebreslassie
(74) *Attorney, Agent, or Firm* — Rabin & Berdo, P.C.

(57) ABSTRACT

The present disclosure relates to a method and a system for collecting and managing terminal use pattern information generated during a process of controlling screen display of a user terminal for eye protection and management. The method, according to the present disclosure, comprises the steps of: measuring a distance between a user terminal and a user; measuring a use time of the user terminal; converting and processing image information displayed on a screen of the user terminal by a predetermined image processing method, when the distance and/or the use time satisfy/satisfies a predetermined condition; and collecting terminal use pattern information comprising at least one of image conversion processing information, distance, and use time when a predetermined reaction is sensed from a user.

15 Claims, 6 Drawing Sheets

(56) References Cited

U.S. PATENT DOCUMENTS

2017/0127055 A1    5/2017  Khabiri et al.
2020/0051522 A1*   2/2020  Lee ........................ G09G 5/003

FOREIGN PATENT DOCUMENTS

| JP | 2017514186 A | 6/2017 |
| KR | 1020090111131 A | 10/2009 |
| KR | 101383870 B1 | 4/2014 |
| KR | 1020140076666 A | 6/2014 |
| KR | 1020140141100 A | 12/2014 |
| KR | 1020150139745 A | 12/2015 |
| KR | 1020160074388 A | 6/2016 |
| KR | 1020170085835 A | 7/2017 |

* cited by examiner

TERMINAL USE PATTERN INFORMATION COLLECTION MANAGEMENT METHOD AND SYSTEM

TECHNICAL FIELD

The present disclosure relates to a terminal use pattern information collection management method and system, and more particularly, to a method and a system for collecting and managing terminal use pattern information generated during a process of controlling screen display of a user terminal for eye protection and management of a user.

BACKGROUND ART

Recently, the advancement in the information and communication technology has enabled a wide spread of mobile communication terminals. The mobile communication terminal can provide not only a telephone function, but also various services desired by a user using various applications.

However, when using the service provided by the mobile communication terminal, the user stares at the screen unconsciously and unknowingly at a short distance for a long time continuously and repeatedly, while having a greatly reduced number of blinks of the eyes.

As such, excessive use of the eye may increase eye fatigue as well as cause dry eyes. In addition, when the dryness of the eyes is increased, there is a problem that the vision is blurred and the eyesight is greatly reduced. Further, the continuing work habit of staying close to the terminal for a long time increases the probability of developing myopia. Recently, statistics have continuously indicated a steep increase in the prevalence rate of myopia in East Asia, and, in particular, high myopia increases the risk of developing ophthalmic diseases such as retinal detachment, retinal tear, myopia macular degeneration, and the like.

In recent years, as the age group using the mobile communication terminals becomes increasingly younger, infants or children with less self-control are also experiencing a deterioration in eyesight, and therefore, there is a need for a technology that can automatically stop or restrict the operation when time of continuously using the mobile communication terminals by the infants or the children exceeds a certain time.

However, the related method of simply stopping or restricting the operations according to the use time of the mobile communication terminal has not been very helpful in reducing the deterioration in eyesight.

DETAILED DESCRIPTION OF THE INVENTION

Technical Problem

Therefore, the technical problem to be solved by the present disclosure is to provide a method and a system for collecting and managing terminal use pattern information generated during a process of controlling a screen display of a user terminal for eye protection and management of a user, and determining and managing a health state of the eye of the user based on the collected terminal use pattern information.

Further, in addition to the objects explicitly mentioned herein, the present disclosure includes other objects that may be achieved from the configuration of the present disclosure described below.

Technical Solution

According to an embodiment of the present disclosure, there is provided a terminal use pattern information collection management method, which may include measuring a distance between a user terminal and a user; measuring a use time of the user terminal; converting and processing image information displayed on a screen of the user terminal by a predetermined image processing method, when at least one of the distance and the use time satisfies a predetermined condition; and collecting terminal use pattern information comprising at least one of image conversion processing information, distance, and use time when a predetermined reaction is sensed from a user.

The predetermined condition may be set such that the distance is less than a reference distance and the use time is equal to or greater than a reference time.

The predetermined image processing method may include increasing or decreasing the image information in steps from an original size as time passes, and the image conversion processing information may include an increase ratio or a decrease ratio of the image information at a time when the reaction is sensed.

The predetermined image processing method may include increasing a degree of blurring of the image information in steps as time passes, and the image conversion processing information may include the degree of blurring of the image information at the time when the reaction is sensed.

The predetermined image processing method may include increasing a range of blurring or darkening the image information in steps from an edge as time passes, and the image conversion processing information may include information on a range of the image information that is blurred or darkened at the time when the reaction is sensed.

The predetermined image processing method may include processing the image information in a predetermined color, and the image conversion processing information may include information on the predetermined color.

The method may further include displaying the image information in an original state when the distance between the user terminal and the user reaches or exceeds a reference distance.

The reaction may include the distance reaching or exceeding a reference distance, or an input of a user operation that is opposite to the converting and processing.

The method may further include determining a health state of an eye of a user based on the collected terminal use pattern information.

According to an embodiment of the present disclosure, there is provided a terminal use pattern information collection management system, which may include a service server that receives terminal use pattern information collected by a user terminal, in which the user terminal converts and processes image information displayed on a screen by a predetermined image processing method when at least one of a distance between a user terminal and a user and a user terminal use time meets a predetermined condition, According to another embodiment of the present disclosure for solving the technical problem described above, there is provided a user terminal, which may include a distance sensor unit that senses information for measuring a distance between a user terminal and a user, and a controller that measures a use time of the user terminal, converts and processes image information displayed on a screen of the user terminal by a predetermined image processing method when at least one of the distance and the use time meets a predetermined condition, and collects terminal use pattern information including at least one of image conversion processing information, the distance, and the use time when a predetermined reaction is sensed from the user.

Advantageous Effects

According to the present disclosure, it is possible to collect and manage terminal use pattern information generated during a process of controlling a screen display of a user terminal for eye protection and management of a user, and determine and manage a health state of the eye of the user based on the collected terminal use pattern information.

In addition, when the user uses the user terminal at a close distance for a long time, while the information that the user is viewing is continuously provided, the information displayed on the screen is increased or decreased in size in steps from the original size and displayed, which may cause the user to voluntarily stay away from the user terminal.

In addition, when the user terminal is used at a close distance for a long time, the information displayed on the screen of the user terminal may be displayed out of focus as if it would appear to those with myopia, thereby reminding and warning the user. In other words, by showing a picture that may indicate actual symptoms of myopia that may occur to the user, it is possible to provide the user with more accurate information and alertness.

Meanwhile, the effects of the present disclosure are not limited to those described above, and other effects that may be derived from the constitution of the present disclosure described below are also included in the effects of the present disclosure.

MODE FOR THE INVENTION

Hereinafter, preferred embodiments of the present disclosure will be described in detail with reference to the accompanying drawings so that those with ordinary knowledge in the art may easily achieve the present disclosure.

Figure 1:
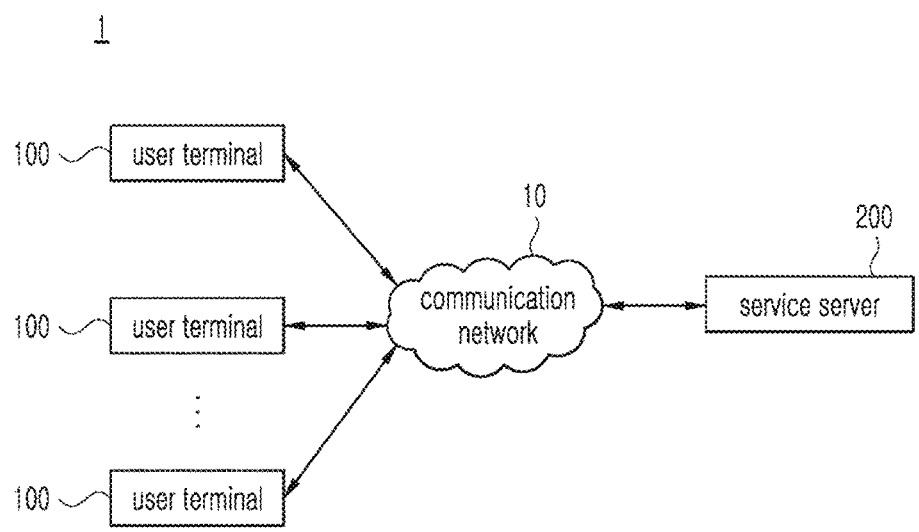
FIG. 1 is a block diagram of a terminal use pattern information collection management system according to an embodiment of the present disclosure.

FIG. 1 is a block diagram of a terminal use pattern information collection management system according to an embodiment of the present disclosure.

Referring to FIG. 1, the system 1 according to the present disclosure may include a plurality of user terminals 100 and a service server 200.

The user terminals 100 and the service server 200 may exchange various information and data through a communication network 10.

The communication network 10 may include various data communication networks including Local Area Network (LAN), Metropolitan Area Network (MAN), Wide Area Network (WAN), internet, 3rd Generation (3G), 4th Generation (4G), Wi-Fi, Wireless Broadband Internet (WIBRO), or Long Term Evolution (LTE), either wired or wireless, and with any communication method.

The user terminals 100 may include a terminal such as smart phone, tablet personal computer (PC), personal digital assistant (PDA), web pad, and the like, which includes a memory means and has a computing capability by mounting a microprocessor. The user terminals 100 may be installed with various applications to provide various services to a user.

When at least one of a distance between the user terminal and the user, and the user terminal use time satisfies a predetermined condition, the user terminals 100 may convert and process the image information displayed on a screen by a predetermined image processing method.

The user terminals 100 may collect terminal use pattern information and provide the same to the service server 200. The 'terminal use pattern information' as used herein may include image conversion processing information, and information on the distance between the user terminal and the user, and the user terminal use time, and the like. The image conversion processing information may include information on details of the conversion of the image information displayed on the screen of the user terminals 100 by a predetermined image processing method. The terminal use pattern information and the image conversion processing information will be described in more detail below.

The service server 200 may collect the terminal use pattern information transmitted from the plurality of user terminals 100, and analyze the collected terminal use pattern information to generate information for managing the state of the eye of the user. For example, in order to predict a maximum total hours of use in a day that should be kept to prevent myopia, the service server 200 may analyze the total use time by the user and measure the degree of myopia progression to collect the data of several people and set a reference point.

The service server 200 may also store the terminal use pattern information transmitted from the user terminal 100 to collect the terminal use pattern information of a predetermined group. For example, in a case when dad, mom, child 1, and child 2 each have a user terminal, a family group may be generated. Accordingly, the terminal use pattern information corresponding to each family member is transmitted to the service server 200, so that the use pattern information of the family group may be analyzed, and a method for managing the eyes of the family group may be coached based on the analyzed result.

Figure 2:
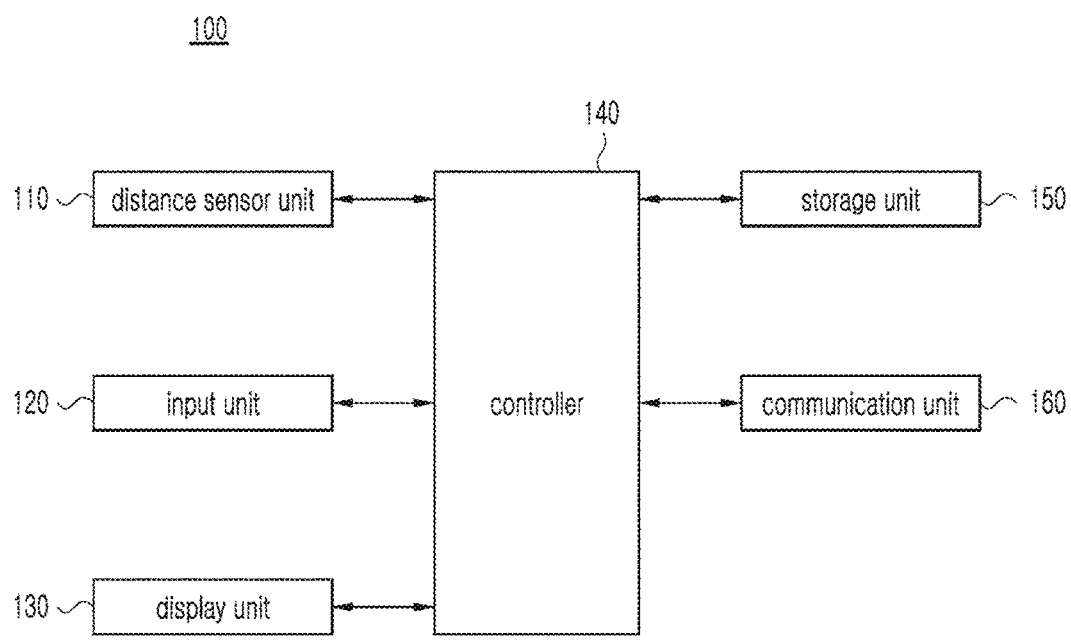
FIG. 2 is a diagram showing a detailed configuration of the user terminal of FIG. 1.

FIG. 2 is a diagram showing a detailed configuration of the user terminal of FIG. 1.

Referring to FIG. 1, the user terminal 100 may include a distance sensor unit 110, an input unit 120, a display unit 130, a controller 140, a storage unit 150, and a communication unit 160.

The distance sensor unit 110 serves to sense information for measuring a distance between the user terminal 100 and the user. For example, the distance sensor unit 110 may be implemented with a camera to obtain an image of a face of the user. The distance between the user terminal 100 and the user may be measured by recognizing eyes, nose, mouth, and the like in the face image of the user captured by the camera. The method for obtaining the distance between the camera and the user using the user face image may be adapted from various known methods. The distance sensor unit 110 may be implemented with an ultrasonic sensor or an optical sensor (infrared ray) and the like. In addition to those described above, the distance sensor unit 110 may be implemented with various devices capable of measuring a distance between the user terminal 100 and the user.

The input unit 120 may serve to receive, from the user, a command relating to an operation of the user terminal 100. The input unit 120 may be implemented with a touch pad, a touch screen, various physical buttons, a microphone, an inertial sensor, and the like.

The display unit 130 serves to display, on the screen, the information relating to the operation of the user terminal 100. The display unit 130 may be implemented with a display module such as LCD panel, OLED panel, and the like.

The controller 140 may be implemented with a central processing unit (CPU) and an operating system, and serves to control various operations of the user terminal 100. For example, the controller 140 may be implemented by using CPU and Android platform. In particular, according to the present disclosure, when the distance between the user terminal 100 and the user is less than a reference distance, and the use time of the user terminal 100 is equal to or greater than a reference time, the controller 140 may operate in an eye protection mode for protecting the eyes of the user.

For example, when determining that the user uses the user terminal 100 at a close distance for a long time, while continuously providing the information that the user has been viewing, the controller 140 displays information displayed on the screen of the user terminal 100 in an increased or decreased size from the original size so as to cause the user to voluntarily move away from the user terminal 100. Of course, in addition to increasing or decreasing the size of the screen, when determining that the user uses the user terminal 100 for a predetermined time or longer at a distance less than a predetermined distance, the controller 140 may operate in the eye protection mode and perform image processing on the image information output on the screen by a predetermined method and output the same so as to cause the user to voluntarily move away from the user terminal 100.

When the distance between the user terminal and the user is equal to or greater than the reference distance, the controller 140 may redisplay the image information in the original form. When the user changes the distance between the user terminal 100 to a certain distance or farther and maintains at that distance, the controller 140 adjusts the size of the information of the screen back to the original form and outputs the same, so that the distance between the user and the user terminal 100 may be maintained constant.

Meanwhile, the controller 140 may display a motion image on the screen when the terminal use time reaches or exceeds a reference time. Alternatively, the controller 140 may receive setting by the user about a continuous use time and display the use time at a predetermined interval. For example, when the continuous use time is set to 50 minutes, a timer may be activated to indicate the duration of time the user terminal has been continuously used so that the user can recognize it, and, as the elapse of the continuous use time is imminent, may messages such as "10 minutes before the continuous use time expires" may be displayed.

In addition, when exceeding the continuous use time, the controller 140 may cause the screen itself to automatically turn green or display a moving image to guide the user to blink the eye and take rest. For example, an eye exercise video may be provided so that the user may blink or take eye exercise, and then the normal screen may be displayed again when the eye exercise video ends.

The storage unit 150 stores various data and programs necessary for the operation of the user terminal 100 and provides the same according to a request of the controller 140. The storage unit 150 may be implemented with a memory module such as a hard disk, a RAM, a ROM, a flash memory, or a solid state drive (SDD).

The communication unit 160 may serve to support exchange of various information and data between the user terminal 100 and an external device, and may include a wired/wireless communication module for this purpose.

Figure 3:
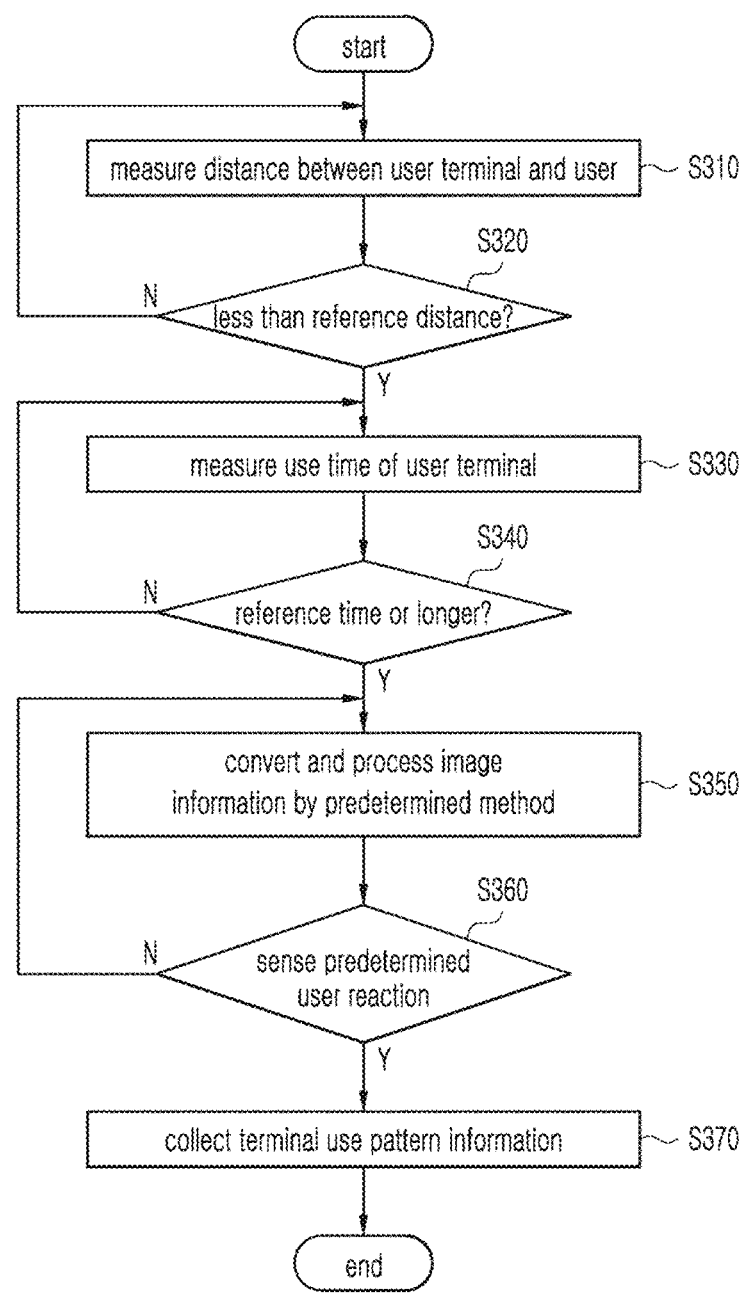
FIG. 3 is a flowchart provided to explain an operation of a terminal use pattern information collection management system according to an embodiment of the present disclosure.

FIG. 3 is a flowchart provided to explain an operation of a terminal use pattern information collection management system according to an embodiment of the present disclosure.

Referring to FIGS. 1 to 3, the controller 140 measures a distance between the user terminal 100 and the user based on the information sensed by the distance sensor unit 110 (S310).

Thereafter, when the distance between the user terminal and the user is less than a predetermined reference distance (S320—Y), the controller 140 may measure the use time of the user terminal from the time when the distance is less than a reference distance (S330).

Next, when the use time of the user terminal reaches or exceeds the reference time since the use time was less than the reference time (S340—Y), the controller 140 may convert and process the image information displayed on the screen of the user terminal 100 by a predetermined image processing method (S350).

At operation S350, various image processing methods may be applied as shown in FIGS. 4 to 6 below.

FIG. 4 shows the image information displayed on a screen being increased in size in steps according to an embodiment of the present disclosure.

Figure 4A:
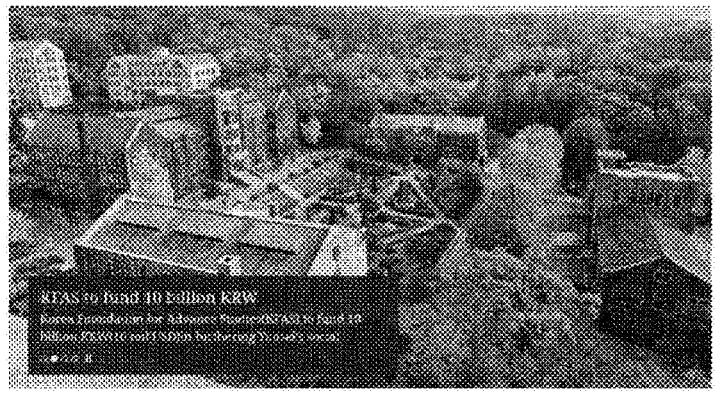
FIG. 4 shows the image information displayed on a screen being increased in size in steps according to an embodiment of the present disclosure.

Referring to FIG. 4, when the user has just started to use the user terminal 100 or at an early stage of using the user terminal 100, information having the original size may be displayed on the screen of the user terminal 100, as shown in FIG. 4A. The 'original size' refers to the size of information such as texts, images, or photos as set in the user terminal 100 itself, or the size previously adjusted and set by the user, which is the size of information normally output from the screen when the user uses the user terminal 100.

However, when the user terminal 100 is used at a close distance for a long time, not only eye fatigue is increased but also the eyes are dried and the vision is blurred, so the user gets closer to the screen to see better.

When determining that the user uses the user terminal 100 at a close distance for a long time, the controller 140 may operate in the eye protection mode to increase the size of the information displayed on the screen from the original size and display the result so that the user may naturally move away from the user terminal 100. When the information displayed on the screen is increased in size from the original size, since the information viewable on the screen is not sufficient, the user has no choice but to ensure a sufficient distance from the user terminal 100 to view the information on the screen.

Figure 4B:
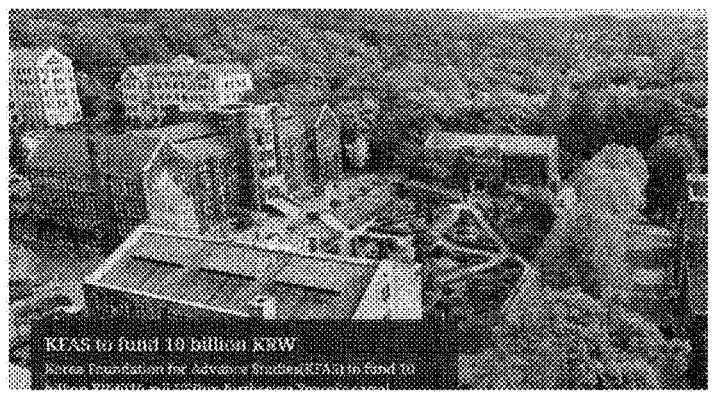

At this time, the ratio of increasing the size of the information on the screen from the original size may be increased in steps as time passes. For example, when the eye protection mode is started at an early stage of the operation time, the information displayed on the screen may be slightly increased in size and displayed as shown in FIG. 4B, and then, when the gaze of the user stays on the screen while the user maintains the close distance to the user terminal 100 for a certain amount of time, the information displayed on the screen may be increased in size in steps to be larger than the information shown in FIG. 4B and displayed. In addition, when the user uses the device in very close proximity to the user terminal 100 for a long time, the information displayed on the screen may be greatly increased in size so that sufficient information may not be viewable on the screen, as shown in FIG. 4C.

Figure 4C:
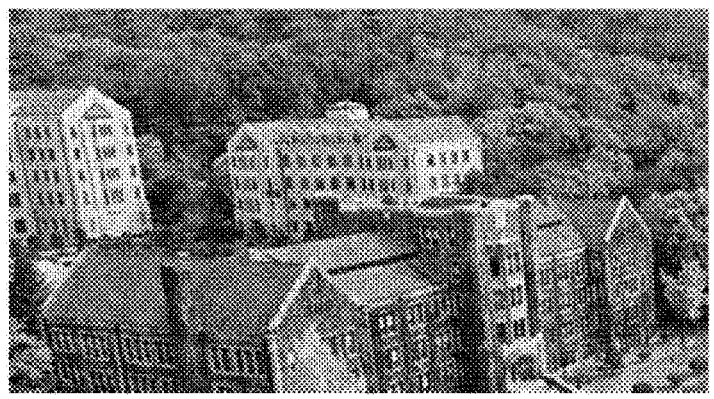

It is needless to say that, according to the situation, while the information on the screen may be displayed in a rapidly increased size from the original size in a short time, the information may be further subdivided than those shown in FIGS. 4B and 4C and the size of the information may be increased in steps so that the user does not recognize it, which may naturally protect the eyes of the user, while allowing the user to use the user terminal 100 without having discomfort. At this time, the information increase ratio of increasing the information in steps without causing the user to perceive the same may be obtained through learning or experiments.

As described above, when the user terminal 100 is used at a close distance for a long time, while the information that the user is viewing is continuously provided, the information on the screen may be increased in size in steps from the original size as time passes to cause the user to voluntarily move away from the user terminal 100.

In addition, the controller 140 may increase the size of the information based on a location corresponding to the direction of the user's gaze. For example, when the user is looking at the information on the real-time rising rank in the Naver (www.naver.com), the controller 140 may increase the size of the information based on the real-time rising rank. As described above, the controller 140 increases the size based on the location where the user's gaze is directed, so that the user may not lose the information that he or she is viewing.

Meanwhile, according to an embodiment, the controller 140 may operate in the eye protection mode to decrease the size of the information displayed on the screen from the original size and display the result. At this time, the ratio of decreasing the size of the information on the screen from the original size may be increased in steps as time passes. In addition, the information decrease ratio of decreasing the information in steps without causing the user to perceive the same may be obtained through learning or experiments.

FIG. 5 shows the image information displayed on a screen being blurred in steps according to an embodiment of the present disclosure.

Referring to FIG. 5, instead of increasing in steps the size of the information to be displayed on the screen, the controller 140 may also increase the degree of blurring of the image information in steps as time passes. In this example, the 'blurring' refers to processing an image so that the image appears out of focus, which is similar to the objects seen out of focus to people with myopia.

Figure 5A:
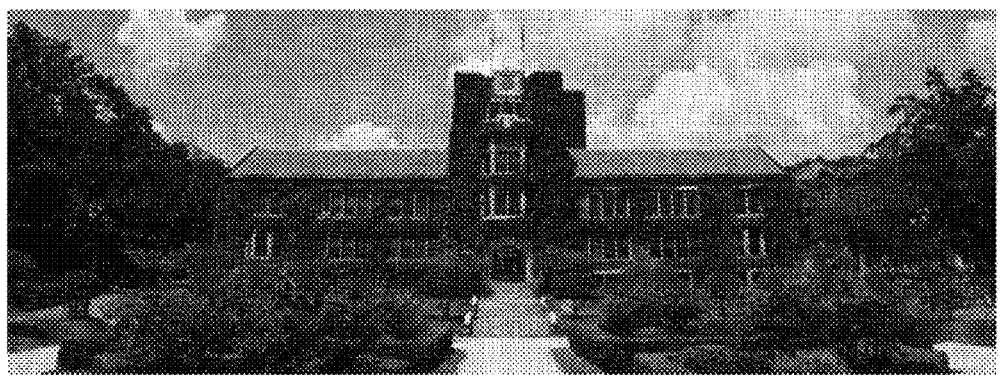
FIG. 5 shows the image information displayed on a screen being blurred in steps according to an embodiment of the present disclosure.
Figure 5B:
Figure 5C:

FIG. 5A illustrates a screen showing the information of the normal form, and FIGS. 5B and 5C illustrate screens showing the information that the degree of blurring is increased in steps. According to an embodiment, the degree of increasing the blurring of the information may be further subdivided than those shown in FIGS. 5B and 5C.

When the just has just started using the user terminal 100 or at an early stage of using the user terminal 100, the normal information that is in focus may be displayed on the screen of the user terminal 100 as shown in FIG. 5A. Then, when the distance between the user and the user terminal 100 is less than a reference distance, and the use time of the user terminal 100 is equal to or greater than a reference time, as shown in FIGS. 5B and 5C, the degree of blurring may be increased in steps so that the information displayed on the screen may be displayed out of focus, which is similar to that seen by those with myopia, thereby reminding and warning the user. As described above, the controller 140 may show a picture that may indicate actual symptoms of myopia that may occur to the user, to provide the user with more accurate information and alertness.

FIG. 6 shows the image information displayed on a screen being darkened in steps from an edge, according to an embodiment of the present disclosure.

Figure 6A:
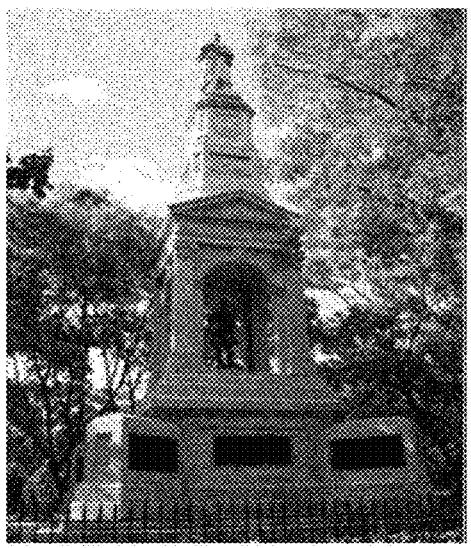
FIG. 6 shows the image information displayed on a screen being darkened in steps from an edge, according to an embodiment of the present disclosure.
Figure 6B:
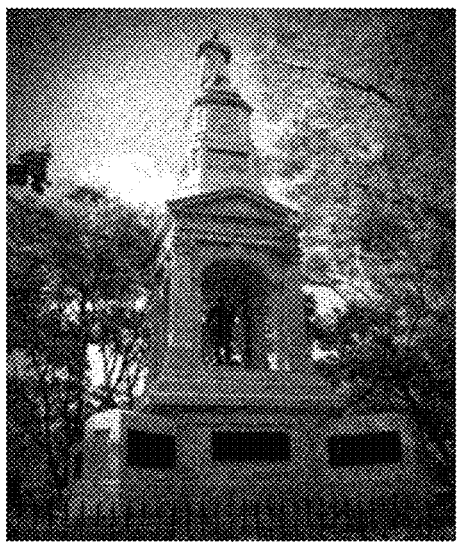
Figure 6C:

Referring to FIG. 6, instead of stepwise increasing the size, or increasing the degree of blurring of the information displayed on the screen, the controller 140 may cause the image information to be darkened in steps from the edge as time passes. According to an embodiment, the degree of darkening the information in steps from the edge may be further subdivided than those shown in FIGS. 6B and 6C.

As myopia progresses, a decrease in the vision due to glaucoma may also be present. FIG. 6A shows the image information displayed in a normal form, and FIGS. 6B and 6C show the effect of reducing the vision of the user by processing the image information to be darkened in steps from the edge.

Meanwhile, according to an embodiment, instead of processing the image information to be darkened in steps from the edge of the image information in FIG. 6, it is also possible to process the image information to be blurred in steps from the edge.

As described above, by showing a picture that may indicate actual symptoms of myopia that may occur to the user, it is possible to provide the user with more accurate information and alertness.

Meanwhile, in addition to the methods described above, various image processing methods may be selected.

For example, the controller 140 may prevent the information from being output on the screen or display the information output on the screen in black and white. In addition, the controller 140 may process the image information in a color preset by a user and output the result. For example, when the user sets a red color in advance which he or she dislikes most, the controller 140 may display the image information in red only. The image information may processed in colors that the user does not like, resulting in an effect that the user stays away from the user terminal 100.

Meanwhile, the controller 140 may output a warning message for guiding the user to stay away from the user terminal. Further, rather than simply outputting a warning message, for example, the information on the screen may be displayed as if it would appear to people with myopia, along with a message stating "Continued watching at a close distance can cause myopia and you may see this."

Referring to FIG. 3 again, after processing the image information by a predetermined method at operation S350, when a predetermined reaction is sensed from the user (S360—Y), the controller 140 may collect image conversion processing information, and terminal use pattern information including a distance between the user terminal and the user, a user terminal use time, and the like (S370). The image conversion processing information collected at operation S370 may include the information from the image processing performed at previous operation S350. The image conversion processing information may include information on an increase ratio, a decrease ratio, and a degree of blurring the image information at the time a predetermined reaction is sensed from the user, and a range of the image information that is blurred or darkened, and the like, that is collected at a time when a predetermined reaction is sensed from the user.

Of course, the terminal use pattern information may also include the image conversion processing information, the distance between the user terminal and the user, the user terminal use time, and the like, that is collected from a predetermined period of time before and after the predetermined reaction is sensed from the user. For example, by collecting information about: the information increase ratio when the user reacted; how close the user approached the user terminal 100 and how far he or she was away from the same; or how long has elapsed since the use of the user terminal 100 when the user moved close to or away from the user terminal 100 than the reference distance, it is possible to analyze the collected terminal use pattern information to determine the state of the eye of the user. In addition, the terminal use pattern information may further include an initial distance or viewing pattern information at the time when the user terminal 100 starts to be used, and may be used to accurately determine the eye state of the user.

At operation S360, the predetermined reaction may be that, after the original image information is converted by a predetermined method and displayed, the user feeling inconvenience moves away from the user terminal 100 by more than a reference distance. Alternatively, at operation S350, a user operation opposite to the conversion processing may be input. For example, it may be an operation for decreasing the enlarged image, or the like.

Meanwhile, after processing the image information by the predetermined method at operation S350, when the distance between the user terminal and the user reaches or exceeds the reference distance (S380—Y), the controller 140 may display the image information converted at operation S350 back in the original state (S390).

The controller 140 may determine a health state of the eye of the user based on the collected terminal use pattern information. The controller 140 may determine the health state of the eye of the user by analyzing the collected terminal use pattern information, and may be configured to directly determine the health state of the eye of the user through a program prepared in advance in the controller 140.

In addition, the controller 140 transmits the terminal use pattern information to the service server 200 and receives the health state of the eye of the user analyzed by the service server 200 to provide the same the user. That is, the user may be provided with information about the health state of his or her eye which is medically analyzed directly by the doctor.

The service server 200 may learn a prediction model of the health state of the eye according to the terminal use pattern of the user by using the big data established with the terminal use pattern information collected and transmitted from the user terminal 100. The service server 200 may provide the user terminal 100 with a result of predicting the health state of the eye of the user based on the prediction model of the health state of the eye.

Embodiments of the present disclosure include a computer-readable medium including program instructions for performing various computer-implemented operations. The medium records a program for executing the methods described above. The medium may include program instructions, data files, data structures, and the like, alone or in combination. Examples of such medium include a magnetic medium such as hard disk, floppy disk and magnetic tape, an optical recording medium such as CD and DVD, a floptical disk and a magneto-optical medium, a hardware device configured to store and execute program instructions, such as ROM, RAM, flash memory, etc. Examples of program instructions include machine language codes such as those generated by a compiler, as well as high-level language codes that may be executed by a computer using an interpreter, and so on.

The present disclosure has been described in detail. However, it should be understood that the detailed description and specific examples, while indicating preferred embodiments of the present disclosure, are given by way of illustration only, since various changes and modifications within the scope of the present disclosure will become apparent to those skilled in the art from this detailed description.

The invention claimed is:

1. A terminal use pattern information collection management method comprising:
    measuring a distance between a user terminal and a user;
    measuring a use time of the user terminal by the user;
    converting and processing image information displayed on a screen of the user terminal by a predetermined image processing method when at least one of the distance and the use time satisfies a predetermined condition; and
    when a predetermined reaction is sensed from the user, collecting terminal use pattern information including at least one of image conversion processing information, the distance, and the use time,
    wherein the predetermined image processing method includes increasing or decreasing the image information from an original size in incremental steps as time passes by, and the image conversion processing information includes an increase ratio or a decrease ratio of the image information at a time when the reaction is sensed.

2. The terminal use pattern information collection management method according to claim 1, wherein the predetermined condition is set such that the distance is less than a reference distance and the use time is equal to or greater than a reference time.

3. The terminal use pattern information collection management method according to claim 1, wherein the predetermined image processing method includes increasing a degree of blurring of the image information in incremental steps as time passes by, and
    the image conversion processing information includes the degree of blurring of the image information at the time when the reaction is sensed.

4. The terminal use pattern information collection management method according to claim 1, wherein the predetermined image processing method includes increasing a range of blurring or darkening the image information from an edge in incremental steps as time passes by, and
    the image conversion processing information includes information on a range of the image information that is blurred or darkened at the time when the reaction is sensed.

5. The terminal use pattern information collection management method according to claim 1, further comprising:
    displaying the image information in an original state when the distance between the user terminal and the user reaches or exceeds a reference distance.

6. The terminal use pattern information collection management method according to claim 1, wherein the reaction includes the distance reaching or exceeding a reference distance, or an input of a user operation that opposite to the converting and processing.

7. The terminal use pattern information collection management method according to claim 1, further comprising determining a health state of an eye of a user based on the collected terminal use pattern information.

8. A terminal use pattern information collection management system comprising:
  a user terminal configured to collect terminal user pattern information and to measure a user terminal use time and a distance between the user terminal and a user; and
  a service server that receives terminal use pattern information collected by the user terminal, wherein the user terminal converts and processes image information displayed on a screen by a predetermined image processing method when at least one of the distance between the user terminal and the user and the user terminal use time satisfies a predetermined condition,
  wherein the terminal use pattern information is collected when a predetermined reaction is sensed from the user, and
  the terminal use pattern information includes at least one of image conversion processing information, the distance, and the use time,
  wherein the predetermined image processing method includes increasing or decreasing the image information from an original size in incremental steps as time passes by, and the image conversion processing information includes an increase ratio or a decrease ratio of the image information at a time when the reaction is sensed.

9. The terminal use pattern information collection management system according to claim 8, wherein the predetermined condition is set such that the distance is less than a reference distance and the use time is equal to or greater than a reference time.

10. The terminal use pattern information collection management system according to claim 8, wherein the predetermined image processing method includes increasing a degree of blurring of the image information in incremental steps as time passes by, and
  the image conversion processing information includes the degree of blurring of the image information at the time when the reaction is sensed.

11. The terminal use pattern information collection management system according to claim 8, wherein the predetermined image processing method includes increasing a range of blurring or darkening the image information from an edge in incremental steps as time passes by, and the image conversion processing information includes information on a range of the image information that is blurred or darkened at the time when the reaction is sensed.

12. The terminal use pattern information collection management system according to claim 8, wherein the user terminal displays the image information in an original state when the distance between the user terminal and the user reaches or exceeds a reference distance.

13. The terminal use pattern information collection management system according to claim 8, wherein the reaction includes the distance reaching or exceeding a reference distance, or an input of a user operation that opposite to the converting and processing.

14. The terminal use pattern information collection management system according to claim 8, wherein the service server determines a health state of an eye of a user based on the collected terminal use pattern information.

15. A user terminal comprising:
  a distance sensor unit configured to sense information for measuring a distance between a user terminal and a user; and
  a controller configured to measure a use time of the user terminal, convert and process image information displayed on a screen of the user terminal by a predetermined image processing method when at least one of the distance and the use time satisfies a predetermined condition, and collect terminal use pattern information including at least one of image conversion processing information, the distance, and the use time when a predetermined reaction is sensed from the user,
  wherein the predetermined condition is set such that the distance is less than a reference distance and the use time is equal to or greater than a reference time, and
  the predetermined image processing method includes increasing or decreasing the image information from an original size in incremental steps as time passes by, and
  the predetermined image processing method includes at least one of increasing a degree of blurring the image information in incremental steps as time passes by, and increasing a range of blurring or darkening the image information from an edge in incremental steps as time passes by, and
  the image conversion processing information includes at least one of: an increase ratio and a decrease ratio of the image information; a degree of blurring the image information at the time when the reaction is sensed; and a range of the image information that is blurred or darkened at the time when the reaction is sensed.

* * * * *